US010576180B2

(12) United States Patent
Caunt et al.

(10) Patent No.: US 10,576,180 B2
(45) Date of Patent: Mar. 3, 2020

(54) DISINFECTION OF A CONTAMINATED ENVIRONMENT

(71) Applicant: GB Sciences LLC, Lawrenceville, GA (US)

(72) Inventors: Philip Caunt, Cardiff (GB); Deborah Williams, Cardiff (GB)

(73) Assignee: GB Sciences LLC, Lawrenceville, GA (US)

( * ) Notice: Subject to any disclaimer, the term of this patent is extended or adjusted under 35 U.S.C. 154(b) by 257 days.

(21) Appl. No.: 15/470,018

(22) Filed: Mar. 27, 2017

(65) Prior Publication Data
US 2017/0197005 A1    Jul. 13, 2017

Related U.S. Application Data

(63) Continuation of application No. 10/566,542, filed as application No. PCT/GB2004/003289 on Jul. 29, 2004, now abandoned.

(30) Foreign Application Priority Data

Jul. 30, 2003 (GB) .................................. 0317862.1

(51) Int. Cl.
| A61L 9/04 | (2006.01) |
| A61L 9/12 | (2006.01) |
| A61L 9/015 | (2006.01) |
| A61L 9/012 | (2006.01) |
| A61L 9/013 | (2006.01) |
| A61K 8/92 | (2006.01) |
| A01N 35/02 | (2006.01) |
| A61K 8/02 | (2006.01) |
| A61Q 17/00 | (2006.01) |
| A01N 65/00 | (2009.01) |
| A61L 2/16 | (2006.01) |
| A01N 65/28 | (2009.01) |
| A01N 65/24 | (2009.01) |
| B65F 1/00 | (2006.01) |

(52) U.S. Cl.
CPC .............. *A61L 9/04* (2013.01); *A01N 35/02* (2013.01); *A01N 65/00* (2013.01); *A01N 65/24* (2013.01); *A01N 65/28* (2013.01); *A61K 8/0208* (2013.01); *A61K 8/922* (2013.01); *A61L 2/16* (2013.01); *A61L 9/012* (2013.01); *A61L 9/013* (2013.01); *A61L 9/015* (2013.01); *A61L 9/044* (2013.01); *A61L 9/046* (2013.01); *A61L 9/048* (2013.01); *A61L 9/12* (2013.01); *A61Q 17/00* (2013.01); *B65F 1/0026* (2013.01); *Y10T 428/24802* (2015.01); *Y10T 428/31844* (2015.04)

(58) Field of Classification Search
CPC . A61L 9/04; A61L 9/015; A61L 9/044; A61L 9/046; A61L 9/048; A61L 9/12; A61L 9/012; A61L 2/16; A61L 9/013; A61K 8/0208; A61K 8/922; A01N 65/24; A01N 65/28; A01N 35/02; A01N 65/00; A61Q 17/00

See application file for complete search history.

(56) References Cited

U.S. PATENT DOCUMENTS

| 5,081,104 A | 1/1992 | Orson, Sr. |
| 5,403,587 A | 4/1995 | McCue et al. |
| 5,712,237 A | 1/1998 | Stevens |
| 6,019,963 A | 2/2000 | Kling et al. |
| 6,103,683 A | 8/2000 | Romano et al. |
| 6,380,152 B1 | 4/2002 | Julemont et al. |
| 2003/0220223 A1 | 11/2003 | Scheuing et al. |
| 2004/0071588 A1* | 4/2004 | Millan ............... A61L 9/013 422/4 |
| 2004/0147425 A1 | 7/2004 | Castro et al. |
| 2005/0106121 A1 | 5/2005 | Hartman et al. |
| 2013/0064956 A1 | 3/2013 | Zeller et al. |

FOREIGN PATENT DOCUMENTS

| CA | 2495932 A1 | 2/2004 |
| EP | 0870507 A1 | 10/1998 |
| EP | 0965541 A2 | 12/1999 |
| EP | 1146111 A1 | 10/2001 |
| JP | 61268258 A | 11/1986 |
| JP | 62164383 | 10/1987 |
| JP | 63252157 | 10/1988 |
| JP | 04053563 | 2/1992 |
| JP | 05269186 | 10/1993 |
| JP | 10075994 | 3/1998 |
| JP | 2002159567 A | 6/2002 |
| JP | 2002238987 A | 8/2002 |
| JP | 2002301144 A | 10/2002 |
| JP | 2002306583 A | 10/2002 |
| JP | 2002349889 A | 12/2002 |

(Continued)

OTHER PUBLICATIONS

International Search Report for Application No. PCT/GB2004/003289 dated Oct. 14, 2004.

*Primary Examiner* — Cheng Yuan Huang
(74) *Attorney, Agent, or Firm* — Lerner, David, Littenberg, Krumbolz & Mentlik, LLP

(57) ABSTRACT

A formulation to reduce the numbers of bacteria, particularly Gram positive bacteria, in a space such as a waste disposal bin, via the vapour phase, and active over a long period, typically several weeks. The product comprises one or more essential oils or essential oil components plus a mixture of volatile and non-volatile solvents, on a carrier such as a non-woven, sintered plastic or cardboard.

7 Claims, No Drawings

(56) References Cited

FOREIGN PATENT DOCUMENTS

| WO | 9639826 A1 | 12/1996 |
|----|------------|---------|
| WO | 0021364 A2 | 4/2000 |
| WO | 03039713 A1 | 5/2003 |
| WO | 2004014416 A1 | 2/2004 |
| WO | 05011757 A1 | 2/2005 |

* cited by examiner

DISINFECTION OF A CONTAMINATED ENVIRONMENT

CROSS-REFERENCE TO RELATED APPLICATION

This application is a continuation of U.S. application Ser. No. 10/566,542, filed on Dec. 18, 2006, which is the U.S. National Stage filing of PCT/GB2004/003289, filed Jul. 29, 2004, which claims priority of Great Britain Patent Application No. 0317862.1, filed Jul. 30, 2003, the disclosures of which are incorporated herein by reference.

FIELD OF THE INVENTION

This invention relates to a product which prevents proliferation of microorganisms, particularly Gram-positive bacteria such as *Staphylococcus aureus*, within a space, via a vapour action, and which is active for long periods, typically several weeks.

BACKGROUND TO THE INVENTION

In the field of disinfection and sanitisation, there is a general move away from chemical agents, due to concerns regarding the safety and effects of these chemical compounds, or their residues, on the environment. This has led to increased interest in the use of natural compounds as disinfectants in many sectors.

The anti-microbial nature of essential oils is well documented. For example, EP 1146111 discloses a hard surface disinfecting formulation based on cinnamon oil or its actives. The compositions are tested according to European Standard EN1276, which measures anti-microbial performance on a single occasion, and over a contact time of 5 minutes. In addition, as the application is for hard surface disinfection, the anti-microbial activity is by direct contact of the active molecules with the microbes. The use of a wipe is discussed, but no details of other carriers, or the effects of different chemistries of the wipe on anti-microbial performance are given.

WO 96/39826 describes the use of essential oil components such as cinnamic aldehyde and coniferyl aldehyde to disinfect contaminated environments, although no useful performance data for the formulations is provided in the specification.

A number of patent publications have also proposed essential oils and essential oil components as a replacement for the fumigant methyl bromide, for the control of plant pathogens. WO200021364 examines the activity of essential oils from plants native to Turkey, such as *Thymbra spicata*, and although the primary targets are insects and fungi, some anti-bacterial activity is claimed, and methods for small scale, short term assessment of vapour activity of the oils are also described. Of the 70 essential oil components listed in the patent publication, the compound anethole was selected for further studies as a fumigant. In addition, no attempts to control the activity over a time period are described.

Feminine hygiene waste, such as used sanitary towels and tampons, and soiled nappies and incontinence pads, are often disposed of in specialist bins, and several companies offer a service relating to these bins. Typically, the bins remain in service at the customers premises for between 2 and 8 weeks. This represents a particular challenge to a disinfectant or sanitizing system, as waste contaminated with potentially pathogenic organisms is constantly being placed into the bins over a long period, steadily increasing the organic matter loading and constantly adding new pathogenic bacteria, requiring disinfection. Thus, feminine hygiene waste bins provide both an application for the technology, and an ideal demonstration of the advantages and features of the invention.

There is concern about the proliferation of microbes within the bin, and it is felt that this may present a hazard to the customers and operatives of the service companies, and may also lead to the development of unpleasant odours. To combat this, a biocidal system is often used in the bin. Traditionally, this has involved use of a large volume of liquid disinfectant, but this leads to an increased weight of material requiring disposal, and there are also concerns regarding the long-term effectiveness of a liquid system throughout the bin once the material has been absorbed into the sanitary waste at the base. Other systems are based on gas-generating systems which produce, for example, sulphur dioxide which can then penetrate and disinfect waste throughout the bin. There is some doubt about the control of release of the gas, as well as health and safety concerns about sulphur dioxide, which has lead to this technology being banned in a number of countries.

As mentioned above, in the field of disinfection, there is a general move away from chemical agents. Simple low volume disinfectant systems for use in bins, based on essential oils and plant extracts is the subject of EP 0 965 541.

The bacteria used to test the performance of the vapour based products disclosed in EP 0 965 541 were Gram-negative bacteria such as *Salmonella, Pseudomonas* and *Escherichia coli*. Gram-positive bacteria seem generally more resistant to natural plant extracts and essential oils. However, many Gram-positive bacteria are pathogenic. *Staphylococcus aureus* for example, can cause a number of common skin infections, and if ingested, can also cause food poisoning. In addition, the experiments reported in EP 0 965 541 did not reflect the time interval of a bin service, and in particular, did not involve repeated experiments in the same receptacle over an extended time. A truly effective natural product for use in a feminine hygiene waste bin will need to be active against all types of bacteria, and over a time frame which accurately represents the service life of the bin, both to fulfill the role of consumer and operator protection, and to achieve regulatory approval in certain markets. Thus, improving the performance of a product against Gram-positive bacteria and controlling the activity of the product to match the service interval of the bin are major features of the present invention.

SUMMARY OF THE INVENTION

According to one aspect of the present invention a vapour-based product for sanitising and deodorising a space such as waste disposal bin over several weeks, comprises a combination of one or more essential oils or essential oil components, and a combination of volatile and non-volatile solvents, absorbed onto a carrier.

According to a second aspect of the present invention, a vapour-producing formulation comprises a combination of one or more essential oils or essential oil components, and a combination of volatile and non-volatile solvents, in a viscous liquid.

According to a third aspect of the present invention, a formulation as defined above is used to sanitise and deodorise a waste disposal bin.

According to a fourth aspect of the present invention, a waste disposal bin comprises a product or formulation as defined above.

According to a fifth aspect of the present invention, a carrier material has one or more essential oil or essential oil components impregnated thereon, the carrier is a resilient or rigid material having a length of at least 200 mm.

DESCRIPTION OF THE INVENTION

The present invention provides formulations and products for sanitising and deodorising a space, for example a waste disposal bin. The invention makes use of an identified synergy between an essential oil or essential oil component and a mixture of volatile or non-volatile solvents.

Preferred essential oil components for use in this invention, which can be used singly, or in combination, are selected from the group consisting of cinnamaldehyde, cinnamic alcohol, geraniol, linalool, benzaldehyde, anisaldehyde, terpinen-4-ol, amyl-cinnamic aldehyde, hexyl-cinnamic aldehyde and eugenol. Preferred essential oils, which again can be used singly and in combination include tea tree oil, clove leaf oil, clove bud oil, cinnamon leaf oil, cinnamon bark oil, spearmint oil (whether of US or Chinese origin), bergamot oil, marjoram oil, bitter almond oil, lemon tea tree oil, bay oil, origanum oil, lemon oil, pimento berry oil, orange oil, cassia oil and cumin oil.

Such essential oil components and/or essential oils can be absorbed onto certain carriers, such as paper, cardboard, etc., so that the vapour action of the product is controlled over a specified time period.

An important aspect of the present invention is the combination of the active ingredient(s) with a blend of at least two solvents. The solvents in the mixture comprise volatile solvents, particularly lower alcohols, and most preferably iso-propanol, and non-volatile solvents such as water, or glycols, most preferably monopropylene glycol. The solvent mixture has two purposes. Firstly by changing the ratio of volatile to non-volatile solvents, the active life of the product can be manipulated. Higher levels of volatile solvents tend to lead to a large initial burst of anti-microbial activity, but a short active life, whilst increasing the levels of non-volatile solvents tends to slow down the rate of release of the anti-microbial vapour, and increase the active life of the product. The ratio of solvents in the current invention can vary between 10:1 and 1:10 volatile to non-volatile solvents, and more preferably between 3:1 and 1:3.

The solvents have a second effect in terms of a synergistic improvement in the anti-microbial activity of the invention. Although both alcohols such as iso-propanol and ethanol, as well as glycols such as monopropylene glycol are all reported as having anti-bacterial or anti-fungal activities, this is normally in relatively high concentrations in a liquid system. In the present invention, a few grams of each solvent are used, which would not be expected to have a disinfecting effect in a bin of up to 50 litre volume over a 6 to 8 week period. However, when used in combination with the oils and oil fractions, unexpected synergistic effects are found, with the combination having a much larger and longer lasting anti-microbial vapour effect than the components alone.

The present invention has also identified synergistic combinations of essential oils and essential oil components. Certain combinations of an essential oil and an essential oil component have a much greater anti-microbial effect than either component demonstrates when used alone. An example of such a mixture is the combination of cinnamon leaf oil and cinnamic alcohol. Although cinnamic alcohol is present in cinnamon leaf oil, it is not the main fraction of the oil, and is not reported to be anti-microbial. Thus increasing it's concentration in a mixture would not be expected to result in any particular increase in anti-microbial activity of the cinnamon leaf oil.

The active material may be impregnated onto a carrier material to permit release of the antimicrobial vapour over an extended period.

A number of carriers can be used to deliver the active ingredient/solvent mixture. A preferred embodiment is the use of a cellulosic fibre/plastic non-woven sheet. Changing the ratio of cellulosic fibre (a polar material) and plastic (non-polar material) can have an effect on the release rate and release characteristics of the active ingredients, in that the polypropylene will have an attraction for non-polar molecules in the active mixture, and will tend to retain them more strongly, whilst the viscose will tend to attract non-polar materials and hold onto them more strongly. A preferred embodiment of the invention is a cellulose (wood pulp fibre)/polypropylene non woven material of approximately 60 g/m$^2$ weight, manufactured by a hydro-entanglement process, known commercially as Ahlstrom A4459. Other suitable non-woven materials from other sources will be obvious to those skilled in the art.

A further embodiment of the invention is the use of a resilient or rigid material, e.g. cardboard, as the carrier. In one embodiment, the cardboard is in the form of a corrugated or solid card, and has a length at least 200 mm, preferably at least 300 mm and most preferably no more than 1000 mm (e.g. up to 400 mm). The width may be at least 10 mm, more preferably 20 mm, and most preferably less than 50 mm. The dimensions have been chosen so that the cardboard can be used as an insert in a waste bin, with the cardboard standing up within the bin, preventing it from being buried by the waste entering the bin. The cardboard may be placed substantially upright or placed across the diagonal of the bin.

The active ingredient mixture can be placed at one end of the cardboard during the manufacturing process, and if this end was then placed uppermost in the bin, it would further resist being buried by the incoming waste. The cardboard, or other resilient or rigid material, may therefore be in the form of a stick. Other shapes and materials which would achieve these objectives will be apparent to those skilled in the art.

The carrier can also consist of a piece of sintered plastic, for example polyethylene or polypropylene. This material can be manufactured in such a way that it consists of an approximately 50% void volume, and this can be filled with the active mixture, either by passive adsorption or by vacuum techniques. The shape of the material can be a sheet, or a more sophisticated moulding, machining or lamination so that in some way it can be attached to inside the bin or on the lid of the bin.

A further embodiment of the carrier is the use of amorphous silicon dioxide, which can absorb over 50% by weight of the active mixture, and due to the fine particle size, can deliver vapour-releasing particles, each producing the active ingredient throughout the bin.

Any suitable solid carrier, either organic, or inorganic, may also be used as a delivery system for the active/solvent mixture. This can include but is not limited to powders, granules, pellets, blocks, pads, sheets, self adhesive materials or labels, etc.

A further embodiment of the invention involves delivery of the active mixture as a viscous gel. The viscosity of the active mixture can be modified by the addition of viscosity-modifying agents such as cellulose gums, anionic co-polymers etc. A preferred method for increasing the viscosity is the use of amorphous silicon dioxide, for example Aerosil 200 from Degussa AG, which can be added to the liquid in the range 1-9%, and more preferably in the range 6.5-8.5% (w/w). Other suitable viscosity modifying systems will be familiar to those skilled in the art.

The following Examples illustrate the invention.

Example 1

This Example illustrates the fact that cinnamic aldehyde on a carrier can have relatively long lasting anti-microbial properties, as described in WO96/39826, but the addition of the solvent mixture increases the initial activity of the formulation, and also significantly improves the effectiveness in the long term. The solvent mixture alone starts off being very effective, but fades rapidly, and at end of the experiment, it is little better than the untreated control.

The test system consisted of a common type of feminine hygiene waste bin. One bin received 2 g of monopropylene glycol and 6 g of iso-propanol, the second 0.5 g of cinnamic aldehyde, the third 0.75 g of cinnamic aldehyde, the fourth 0.5 g of cinnamic aldehyde, plus 2 g of monopropylene glycol and 6 g of iso-propanol, the fifth 0.75 g of cinnamic aldehyde, plus 2 g of monopropylene glycol and 6 g of iso-propanol. All test solutions were absorbed onto a 20 cm×20 cm piece of a cellulose/polypropylene non woven, namelu, Ahlstrom AH4559. A final bin received no treatment and served as a control.

To begin the experiment, 1 ml of sterile horse serum was added to 9 ml of an overnight culture of the Gram-positive organism *Staphylococcus aureus* NCTC 4163, and 20 μl of this mixture was then pipetted onto 40 sterile Whatman antibiotic discs for each bin. The inoculated discs were placed in individual compartments of Sterilin 25 compartment square Petri dishes, (Sterilin part code 103), and the lids were turned so that they were propped open. The plates were then placed in baskets approximately 15 cm above the base of the bin, and the lid placed on the bin. Following either 24, 48 or 72 hours of exposure to the product vapour (see Table 1), discs were removed from the trays and surviving bacteria counted by decimal dilutions in maximum recovery diluent and plating onto solidified Baird-Parker medium, which is selective for *Staphylococcus* strains, using the Miles and Misra technique. The plates were incubated overnight at 37° C., and then colonies counted on the appropriate dilution. Discs were placed into the units at time zero, after 14 days, 20 days and 35 days, and the number of surviving bacteria on each disc on each occasion was calculated, and the results for the test formulations are shown below:

TABLE 1

| | Surviving bacteria on disc when discs placed in bin | | | |
|---|---|---|---|---|
| | After 0 days (72 hr exposure) | After 14 days (72 hr exposure) | After 20 days (24 hr exposure) | After 35 days (24 hr exposure) |
| Control | $4.0 \times 10^7$ | $2.4 \times 10^6$ | $1.4 \times 10^7$ | $5.8 \times 10^7$ |
| Solvent mixture | $<6.6 \times 10^1$ | $1.3 \times 10^2$ | $3.8 \times 10^6$ | $3.1 \times 10^7$ |
| 0.5 g cinnamic aldehyde | $1.9 \times 10^3$ | $<6.6 \times 10^1$ | $3.2 \times 10^6$ | $7.3 \times 10^5$ |
| 0.75 g cinnamic aldehyde | $5.0 \times 10^2$ | $<6.6 \times 10^1$ | $1.7 \times 10^5$ | $6.5 \times 10^4$ |

TABLE 1-continued

| | Surviving bacteria on disc when discs placed in bin | | | |
|---|---|---|---|---|
| | After 0 days (72 hr exposure) | After 14 days (72 hr exposure) | After 20 days (24 hr exposure) | After 35 days (24 hr exposure) |
| 0.5 g cinnamic aldehyde plus solvent mixture | $<6.6 \times 10^1$ | $<6.6 \times 10^1$ | $7.1 \times 10^5$ | $5.3 \times 10^4$ |
| 0.75 g cinnamic aldehyde plus solvent mixture | $<6.6 \times 10^1$ | $<6.6 \times 10^1$ | $1.3 \times 10^4$ | $3.3 \times 10^2$ |

Example 2

To further illustrate the synergistic effects of mixtures of essential oils and essential oil components, three formulations were prepared, one containing 2 g of cinnamon leaf oil, the second 1 g of cinnamic alcohol and the third both 2 g of cinnamon leaf oil and 1 g of cinnamic alcohol.

The method used was the disc method described in Example 1, except that *Escherichia coil* NCTC8196 was used as the test organism, the discs were placed into the units at time zero, and they were exposed to the product vapour for 72 hours, and MacConkey agar No. 3 was used for enumeration of surviving bacteria. The results for the three test formulations are shown below:

TABLE 2

| | 2 g cinnamon leaf oil | 1 g cinnamic alcohol | 1 g cinnamic alcohol plus 2 g cinnamon leaf oil |
|---|---|---|---|
| Number of bacteria surviving on the disc | $4.9 \times 10^5$ | $1.1 \times 10^5$ | $<6.6 \times 10^1$ |

This experiment clearly illustrates that a combination of the essential oil and the essential oil component is considerably more effective than either constituent alone.

Example 3

A further experiment was conducted to study the effect of varying the solvent ratio in relation to the longevity of the action of the product. Various formulations were prepared, each containing 2 g of cinnamon leaf oil and 1 g of cinnamic alcohol. Each formulation also contained 10 g of the solvent mixture, at varying ratios of iso-propanol to monopropylene glycol.

The test system described in Example 2 was used, in that the organism used was *Escherichia coil* NCTC8196, and the agar used for growth of the organisms was MacConkey agar No. 3. In this example, following 24, 48 and 72 hours of exposure to the product vapour, 5 discs were removed from the trays and placed into 9 ml of nutrient broth. These broths were incubated at 37° C., and then examined for growth after 24 hours. Any broths showing growth were subsequently streaked onto MacConkey agar No. 3, to test for the presence of *E. coli*. Growth on the streak was scored as a positive (i.e. surviving *E. coli* were present on the disc) and no growth as a negative (100% kill of *E. coli* on the disc). The experiment was repeated, in that fresh inoculated discs were placed into the bins at 0, 2, 4, 6 and 8 weeks after the addition of the test formulation, and the results for the varying solvent ratios are shown below:

TABLE 3

| Ratio IPA:MPG | code | 0 weeks | 2 weeks | 4 weeks | 6 weeks | 8 weeks |
|---|---|---|---|---|---|---|
| 1:3 | H | All negative 48 hours | All positive 72 hours | All positive 72 hours | Not tested | Not tested |
| 1:1 | K | All negative 48 hours | All positive 72 hours | All positive 72 hours | Not tested | Not tested |
| 3:1 | V | All negative 48 hours | All negative 24 hours | All negative 48 hours | All negative 48 hours | All negative 72 hours |
| 5:1 | R | All negative 24 hours | All negative 48 hours | All negative 48 hours | Two positive 72 hours | Two positive 72 hours |

The results show that in mixtures containing predominantly monopropylene glycol, the initial performance of the product is acceptable, but the performance rapidly fades over the longer term. Increasing the proportion of iso-propanol to make an equal mixture, shows no improvement, but increasing it again to 3:1 iso-propanol to monopropylene glycol, significantly improves the long term performance of the product, so that it remains active for the desired 8 weeks in the unit. By increasing the amount of iso-propanol even further, to 5:1, the initial performance is improved slightly, but the long term performance is again less acceptable. Thus, the effect of manipulating the ratio on the long term activity of the formulation is demonstrated. A 3:1 ratio is the correct combination for a product active against this bacterium and utilizing these oils, but other oils and other active mixtures may require different proportions of volatile and non-volatile solvents, depending on the characteristics of the active mixture itself.

Example 4

A further illustration of the value of this invention over the prior art is provided in the following Example. A combination of tea tree oil and silicon dioxide was described in EP 0 965 541. This prior art formulation, consisting of 1.2 g of tea tree oil absorbed onto 3.8 g of Sipernat 22 silicon dioxide, was tested against a formulation consisting of 1.2 g of tea tree oil, 4.2 g of monopropylene glycol, 1.8 g of iso-propanol, absorbed onto 5.4 g of Sipernat 22 silicon dioxide in a jar experiment. Three jars were used for each of the two trial formulations and three jars for the control. The two products were each placed into the bottom of three jars, and sanitary towels inoculated with three test bacteria, Salmonella typhimurium, Staphylococcus aureus and Escherichia coli, suspended above the products in separate jars, and the jars sealed. Surviving bacteria in the towels were counted using standard microbiological methods.

TABLE 4

| Organism | Formula | 1 day contact | 2 day contact | 7 day contact |
|---|---|---|---|---|
| Staphylococcus aureus | Prior art | $2.7 \times 10^8$ | $4.7 \times 10^8$ | $<3 \times 10^3$ |
|  | Solvent formulation | $<3 \times 10^3$ | NT | NT |
| Salmonella typhimurium | Prior art | $3.6e8^8$ | $3.7 \times 10^8$ | $<3 \times 10^3$ |
|  | Solvent formulation | $<3 \times 10^3$ | NT | NT |
| Escherichia coli | Prior art | $4.5 \times 10^8$ | $2.9 \times 10^8$ | $<3 \times 10^3$ |
|  | Solvent formulation | $<3 \times 10^3$ | NT | NT |

The data from the prior art formulation is similar to that reported in EP 0 965 541, in that bacteria numbers were reduced in around 7 days exposure to the product vapour. The increased activity of the new formulation, including solvents, is clearly shown, in that bacteria levels are reduced to below detection limits in just one day.

Example 5

One particular embodiment of the present invention involves delivering the active ingredient mixture on a sheet of non-woven fabric. Not only does this make the manufacturing process economic, and the product easy for the end user to dispense, it also improves the anti-microbial performance of the product. An active ingredient mixture, consisting of 2 g of cinnamic aldehyde and 1 g of cinnamon leaf oil, plus a solvent mix of 6 g of monopropylene glycol and of 2 g iso-propanol, was tested in a number of delivery systems. In one sanitary disposal unit, the liquid active itself was placed in a small glass beaker placed in the base of the unit, in a second unit, the active mixture was absorbed onto a 85 mm×55 mm×4 mm thick pure cellulose pad, and in a third, the active was absorbed onto the preferred embodiment, a 20 cm×20 cm piece of a cellulose/polypropylene non-woven, namely Ahlstrom AH4559. A fourth unit had no treatment and thus served as the control.

The test system described in Example 1 was used, i.e. Staphylococcus aureus bacteria on discs. In this Example, the inoculated discs were placed into the units after 10 days, and exposed to the product for 48 hours before the discs were removed and surviving bacteria on each disc were enumerated. The results are shown in the following table 5:

TABLE 5

| Treatment | Surviving bacteria per disc after 48 hours exposure |
|---|---|
| None (control) | $3.0 \times 10^7$ |
| Active mix + solvents in glass beaker | $6.2 \times 10^6$ |
| Active mix + solvents of cellulose pad | $2.5 \times 10^5$ |
| Active mix + solvents on non-woven sheet | $7.2 \times 10^3$ |

Example 6

A further embodiment of the present invention involves delivering the active ingredient mixture on a piece of cardboard. The active mixture consisted of 0.75 g of cinnamic aldehyde, and the cardboard was a B flute corrugated board, and of dimensions 400 mm×20 mm×3 mm. The active mixture was absorbed onto one end of the cardboard, and this end was then placed uppermost in the unit. One sanitary disposal unit received the test system, and a second had no treatment and thus served as the control. The test system described in Example 1 was used, i.e. *Staphylococcus aureus* bacteria on discs. In this example, the inoculated discs were placed into the units at time zero and after 14 days, and exposed to the product for 72 hours before the discs were removed and surviving bacteria on each disc were enumerated. The results are shown in the following table 6:

TABLE 6

| Treatment | Surviving bacteria per disc after 72 hours exposure | |
|---|---|---|
| | Time zero | 14 days |
| None (control) | $2.3 \times 10^7$ | $3.1 \times 10^7$ |
| Active mix on cardboard | $1.3 \times 10^3$ | $3.2 \times 10^4$ |

The results show that cardboard is a further suitable material to deliver the technology.

Example 7

Further embodiments of the present invention involve delivering the active ingredient mixture on a piece of sintered polyethylene, or in a viscous gel, formed by the addition of silicon dioxide. In each case, the active mixture consisted of 1 g of cinnamic aldehyde plus a solvent mix of 6 g of monopropylene glycol and of 2 g iso-propanol. The sintered polyethylene was of dimensions 100 mm×80 mm×3 mm, and had an average pore size of 100 μm and a void volume of approximately 40%. The gel was created by adding 6.5% Aerosil 200, a fumed silicon dioxide produced by Degussa, to the liquid preparation. One sanitary disposal unit received the sintered plastic system, one the gel, and the third unit had no treatment and thus served as the control.

The test system described in Example 1 was used, i.e. *Staphylococcus aureus* bacteria on discs. In this example, the inoculated discs were placed into the units at time zero and after 14 days, and exposed to the product for 72 hours before the discs were removed and surviving bacteria on each disc were enumerated. The results are shown in the following table 7:

TABLE 7

| Treatment | Surviving bacteria per disc after 72 hours exposure | |
|---|---|---|
| | Time zero | 14 days |
| None (control) | $2.3 \times 10^7$ | $3.1 \times 10^7$ |
| Active mix in sintered plastic | $<6.6 \times 10^1$ | $<6.6 \times 10^1$ |
| Active mix in viscous gel | $<6.6 \times 10^1$ | $1.5 \times 10^5$ |

The results show that both embodiments are suitable ways of delivering the technology. Indications from these un-optimised systems are that the sintered plastic is slightly more effective than the viscous gel.

Example 8

A further illustration of the value of the current invention over the prior art is provided below. An active ingredient mixture, consisting of 4 g of cinnamic aldehyde and a solvent mix of 6 g of monopropylene glycol and of 2 g iso-propanol, absorbed onto a 20 cm×20 cm piece of Ahlstrom AH4559 was tested against a formulation containing 1.2 g of tea tree oil absorbed onto 3.8 g of Sipernat 22 silicon dioxide, as described in EP 0 965 541.

The test system described in Examples 1 and 5 was used, i.e. *Staphylococcus aureus* NCTC 4196 bacteria on discs. In this Example, inoculated discs were placed into the units at time zero, and after 4 and 8 weeks, and exposed to the product vapour for 72 hours on each occasion, before the discs were removed and the number of surviving bacteria per disc enumerated. The results are shown in the following table 8:

TABLE 8

| Treatment | Surviving bacteria per disc after 72 hours exposure | | |
|---|---|---|---|
| | Time zero | 4 weeks | 8 weeks |
| Prior art (tea tree oil and silicon dioxide) | $3.6 \times 10^5$ | $1.6 \times 10^7$ | $4.1 \times 10^7$ |
| Present invention (cinnamic aldehyde + solvents on a non-woven sheet) | $<6.6 \times 10^1$ | $<6.6 \times 10^1$ | $<6.6 \times 10^1$ |

The fact that significant anti-microbial results, were obtained, against a Gram positive bacterium over an 8 week period, clearly illustrates the value of the invention over the prior art.

Example 9

A further experiment was conducted to illustrate the effect of using different volatile solvents in place of iso-propanol. An active ingredient mixture, consisting of 1.5 g of cinnamic aldehyde, 0.25 g cinnamon leaf oil and a solvent mix of 3 g of monopropylene glycol and 9 g of each alcohol was used. Five alcohols were tested in total, namely iso-propanol, n-propanol, methanol, ethanol and n-butanol. Each active and solvent mixture was absorbed onto a 20 cm×20 cm piece of Ahlstrom AH4559.

The test system described in Example 1 was used, i.e. *Staphylococcus aureus* NCTC 4196 bacteria on discs. In this Example, inoculated discs were placed into the units at time zero, and after 2, 4 and 6 weeks. Samples were removed from each bin following exposure to the product vapour for 72 hours on each occasion. The discs were removed and placed into 9 ml of nutrient broth. These broths were incubated at 37° C., and then examined for growth after 24 hours. Any broths showing growth were subsequently streaked onto Baird Parker agar, to confirm the presence of *Staphylococcus aureus*. Growth on the streak was scored as a positive (i.e. surviving *Staphylococcus aureus* were present on the disc) and no growth as a negative (100% kill of *Staphylococcus aureus* on the disc). The results are shown in the following table 9:

TABLE 9

| Treatment | Presence of surviving bacteria following 72 hours exposure | | | |
|---|---|---|---|---|
| | Week 0 | Week 2 | Week 4 | Week 6 |
| Control | + + | + + | + + | + + |
| Iso-propanol | − − | − − | − − | − − |
| Methanol | − − | − − | − − | − − |
| Ethanol | − − | − − | − − | − − |

TABLE 9-continued

| Treatment | Presence of surviving bacteria following 72 hours exposure | | | |
|---|---|---|---|---|
| | Week 0 | Week 2 | Week 4 | Week 6 |
| N-Butanol | – – | – – | – – | – – |
| N-Propanol | – – | – – | – – | – – |

These results clearly show that a wide range of alcohols can be used in the present invention.

Example 10

A further experiment was conducted to illustrate the effect of using different glycols in place of mono propylene glycol. An active ingredient mixture, consisting of 1.5 g of cinnamic aldehyde, 0.25 g cinnamon leaf oil and a solvent mix of 3 g of glycol and of 9 g isopropanol was used as standard. Five glycols were tested in total. Each active mixture was absorbed onto a 20 cm×20 cm piece of Ahlstrom AH4559.

The test system described in Examples 1 was used, i.e. *Staphylococcus aureus* NCTC 4196 bacteria on discs. In this Example, inoculated discs were placed into the units at week 1 and removed from each bin following exposure to the product vapour for 24 and 48 hours. The discs were removed and placed into 9 ml of nutrient broth. These broths were incubated at 37° C., and then examined for growth after 24 hours. Any broths showing growth were subsequently streaked onto Baird Parker agar, to test for the presence of *Staphylococcus aureus*. Growth on the streak was scored as a positive (i.e. surviving *Staphylococcus aureus* were present on the disc) and no growth as a negative (100% kill of *Staphylococcus aureus* on the disc). The results are shown in the following table 10:

TABLE 10

| Treatment | Presence of surviving bacteria | |
|---|---|---|
| | T = 24 hours | T = 48 hours |
| Control | + + | + + |
| Diethylene glycol | – – | – – |
| Hexylene glycol | – – | – – |
| Butyl glycol | – – | – – |
| Monoethylene glycol | – – | – – |
| Dipropylene glycol | – – | – – |

These results clearly show that a wide range of glycols can serve as the non-volatile solvent in the present invention.

Example 11

A further illustration of the range of non-volatile solvents useable in the current invention is provided below. An active ingredient mixture, consisting of 2 g of cinnamic aldehyde, 0.25 g cinnamon leaf oil, plus a solvent mix of 3.5 g of water and of 6.5 g iso-propanol, absorbed onto a 22 cm×25 cm piece of Ahlstrom AH4559 was tested using the method described in Examples 1 and 5, i.e. *Staphylococcus aureus* NCTC 4196 bacteria on discs. In this example, inoculated discs were placed into the units at time zero, and after 2, 4, 6 and 8 weeks. Samples were removed from each bin following exposure to the product vapour for 72 hours on each occasion. The discs were removed and surviving bacteria enumerated (Table 11).

TABLE 11

| Treatment: | Surviving bacteria on the discs after 72 hours exposure at: | | | | |
|---|---|---|---|---|---|
| | Time zero | 2 weeks | 4 weeks | 6 weeks | 8 weeks |
| none | 4.72e7 | 5.95e7 | 5.0e7 | 5.4e7 | 6.4e7 |
| Active mix | <67 | <67 | <67 | <67 | <67 |

The fact that significant anti-microbial results, were obtained, against a Gram-positive bacterium over an 8 week period, clearly illustrates the value of this particular embodiment of the invention.

The invention claimed is:

1. A vapour-producing composition for disinfection of a space via the vapour phase, comprising:
   an essential oil component, an essential oil and a mixture of a volatile solvent and a non-volatile solvent absorbed on a carrier,
   wherein the weight ratio of volatile to non-volatile solvent is in the range 10:1 to 1:1,
   wherein the essential oil component is cinnamic aldehyde and the essential oil is cinnamon leaf oil;
   the volatile solvent is iso-propanol;
   the non-volatile solvent is monopropylene glycol,
   wherein when absorbed on the carrier, the composition permits release of the active vapour over a period of up to four weeks.

2. The vapour-producing composition according to claim 1, wherein when absorbed on the carrier, the composition permits release of the active vapour over a period of up to six weeks.

3. The vapour-producing composition according to claim 1, wherein the weight ratio of volatile to non-volatile solvent is 3:1 to 1:1.

4. The vapour-producing composition of claim 1, wherein the carrier is (i) amorphous silicon dioxide, (ii) a non-woven material comprising cellulosic fibers and plastic, or (iii) a resilient or rigid material.

5. The vapour-producing composition of claim 1, wherein the carrier is a resilient or rigid material and is cardboard.

6. The vapour-producing composition of claim 1, wherein the carrier is a resilient or rigid material and has one dimension of at least 200 mm.

7. The vapour-producing composition of claim 1, wherein the composition does not contain water.

* * * * *